US011517286B2

(12) United States Patent
Sato et al.

(10) Patent No.: US 11,517,286 B2
(45) Date of Patent: Dec. 6, 2022

(54) ULTRASONIC PROBE AND ULTRASONIC PROBE ATTACHMENT

(71) Applicant: CANON MEDICAL SYSTEMS CORPORATION, Otawara (JP)

(72) Inventors: Tomohiro Sato, Otawara (JP); Takashi Takeuchi, Otawara (JP); Hiroyuki Shikata, Nasushiobara (JP); Kengo Okada, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/005,380

(22) Filed: Aug. 28, 2020

(65) Prior Publication Data

US 2021/0059641 A1 Mar. 4, 2021

(30) Foreign Application Priority Data

Aug. 30, 2019 (JP) ............................ JP2019-158562

(51) Int. Cl.
*A61B 8/00* (2006.01)
*A61B 8/08* (2006.01)

(52) U.S. Cl.
CPC .......... *A61B 8/4444* (2013.01); *A61B 8/4281* (2013.01); *A61B 8/4494* (2013.01); *A61B 8/461* (2013.01); *A61B 8/488* (2013.01); *A61B 8/5207* (2013.01)

(58) Field of Classification Search
CPC ... A61B 8/4281; A61B 8/4444; A61B 8/4455; A61B 8/4488; A61B 8/4494; A61B 8/461; A61B 8/488; A61B 8/5207
See application file for complete search history.

(56) References Cited

U.S. PATENT DOCUMENTS

2005/0096547 A1* 5/2005 Wendelken .......... A61B 8/4281 600/459
2017/0000459 A1* 1/2017 Shikata ................ A61B 8/4444

FOREIGN PATENT DOCUMENTS

JP 04-138145 A 5/1992
JP 2000-201929 A 7/2000
JP 2014-195497 A 10/2014
JP 2015-080671 A 4/2015

* cited by examiner

*Primary Examiner* — Yi-Shan Yang
*Assistant Examiner* — Alexei Bykhovski
(74) *Attorney, Agent, or Firm* — Oblon, McClelland, Maier & Neustadt, L.L.P.

(57) ABSTRACT

An ultrasonic probe according to an embodiment comprises an ultrasonic-transducer element array, an offset and an exterior member. The ultrasonic-transducer element array is formed by a plurality of ultrasonic transducer elements. The offset is provide on an ultrasonic-transmitting and receiving side of the ultrasonic-transducer element array and includes a contact portion with a subject. The exterior member supports the offset. The offset has at least a first region that is formed by a curved surface having a first curvature and arranged in the middle of the contact portion and a second region that is formed by a curved surface having a second curvature greater than the first curvature and arranged on an edge of the contact portion.

25 Claims, 11 Drawing Sheets

ULTRASONIC PROBE AND ULTRASONIC PROBE ATTACHMENT

CROSS-REFERENCE TO RELATED APPLICATIONS

This application is based upon and claims the benefit of priority from Japanese Patent Application No. 2019-158562, filed on Aug. 30, 2019; the entire contents of which are incorporated herein by reference.

FIELD

Embodiments described herein relate generally to an ultrasonic probe and an ultrasonic probe attachment.

BACKGROUND

An ultrasonic diagnostic apparatus that scans the inside of a subject with ultrasonic waves and, based on reflected waves from the inside of the subject, images the inside of the subject has been disclosed. In such an ultrasonic diagnostic apparatus, the ultrasonic waves are transmitted to the subject by using an ultrasonic probe having a plurality of ultrasonic transducer elements and reflected waves from the relevant subject are received.

In a body contact member in an acoustic irradiation (radiation) direction of the ultrasonic probe, there is a case of arranging a lens member that is an acoustic focusing material and has a curvature in order to achieve an acoustic focusing effect and, although the acoustic focusing effect is not intended, there is a case of arranging an elastic material (hereinafter referred to as "offset") that has no acoustic focusing effect for the purpose of ensuring contact properties with the body, the purpose of improving acoustic characteristics, and the like. Conventionally, in the latter case in which the offset is arranged, the contact surface of a body contact portion (body contact surface) of this offset is a plane surface or a curved surface of constant curvature (or a curved surface for which the cross-section along the longitudinal direction is of a curve having a single curvature) from the point of view of body contact properties.

In a probe that deflects an acoustic path such as a sector probe, a convex probe, and the like, when the body contact surface is of a plane surface or a curved surface of a single curvature, there is a need to ensure the acoustic path in the vicinity of an edge portion of the offset while ensuring the thickness dimension of the offset that is functionally needed. Thus, the offset of the conventional ultrasonic probe and an acoustic radiation opening of the exterior member that supports the relevant offset are ensured to be large.

The conventional ultrasonic probe has a problem in that the footprint of the body contact portion is large because there is a need to ensure that the offset and the acoustic radiation opening of the exterior member that supports the relevant offset are large. In addition, because the acoustic path runs having an angle in the deflection direction in the offset, there is a problem in that the length of the acoustic path in the offset becomes large and the energy loss of sound waves due to in-offset attenuation becomes large.

DETAILED DESCRIPTION

An ultrasonic probe according to an embodiment comprises an ultrasonic-transducer element array, an offset and an exterior member. The ultrasonic-transducer element array is formed by a plurality of ultrasonic transducer elements. The offset is provide on an ultrasonic-transmitting and receiving side of the ultrasonic-transducer element array and includes a contact portion with a subject. The exterior member supports the offset. The offset has at least a first region that is formed by a curved surface having a first curvature and arranged in the middle of the contact portion and a second region that is formed by a curved surface having a second curvature greater than the first curvature and arranged on an edge of the contact portion.

The following describes a first embodiment and a second embodiment with reference to the accompanying drawings. In the following description, constituent elements having substantially identical functions and configurations are denoted by identical reference signs, and their redundant explanations are made only when needed. In addition, the embodiments can be combined with other embodiments or conventional technologies within the scope of not causing contradiction in the configuration.

First Embodiment

Figure 1:
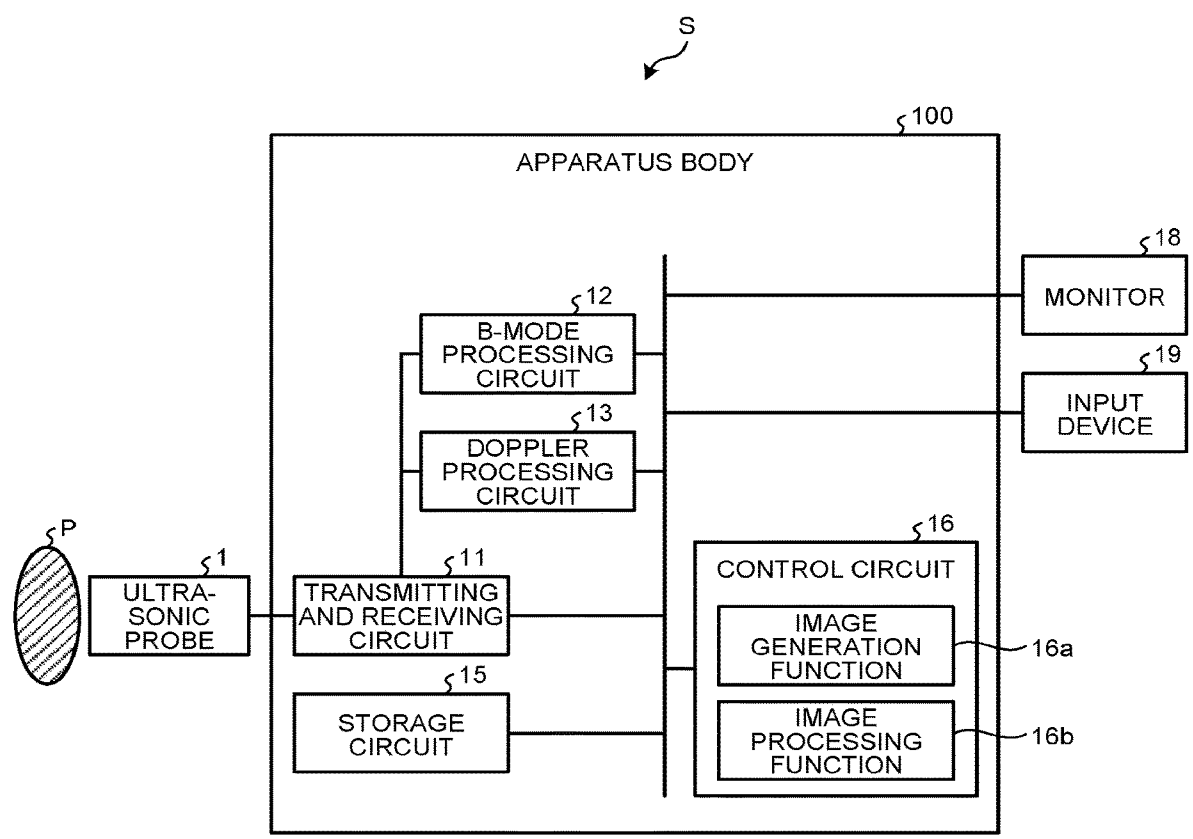
FIG. 1 is a block diagram illustrating one example of a configuration of an ultrasonic diagnostic apparatus equipped with an ultrasonic probe according to a first embodiment.

FIG. 1 is a block diagram illustrating one example of the configuration of an ultrasonic diagnostic apparatus S equipped with an ultrasonic probe 1 according to a first embodiment. As illustrated in FIG. 1, the ultrasonic diagnostic apparatus S in the first embodiment includes the ultrasonic probe 1, an apparatus body 100, a monitor 18, and an input device 19. The ultrasonic probe 1, the monitor 18, and the input device 19 are connected to the apparatus body 100 so as to be able to perform communication. A subject P is not included in the configuration of the ultrasonic diagnostic apparatus s.

The ultrasonic probe 1 is brought into contact with a subject, transmits ultrasonic waves to the relevant subject, and receives reflected waves from the subject due to the transmitted ultrasonic waves. The ultrasonic probe 1 is a two-dimensional ultrasonic probe having a transducer element array for which a plurality of ultrasonic transducer elements (ultrasonic transducers) are two-dimensionally arranged in a lattice form, for example.

The ultrasonic transducer elements generate ultrasonic waves on the basis of drive signals supplied from the device body 100. The ultrasonic transducer elements receive reflected waves from the subject P and convert them into electrical signals (echo signal). The ultrasonic probe 1 further includes an offset, an exterior member that supports the offset, a backing material that prevents the ultrasonic waves from propagating from the ultrasonic transducer elements toward the rear, and the like (see FIG. 9).

The configuration of the ultrasonic probe 1 will be described in detail later.

The monitor 18 displays a GUI (graphical user interface) for a user of the ultrasonic diagnostic apparatus S to input various setting requests by using the input device 19 and displays ultrasonic images and the like generated in the apparatus body 100.

The input device 19 is implemented by a trackball, switches, dials, a touch command screen, footswitches, a joystick, and the like. The input device 19 receives various setting requests from the user of the ultrasonic diagnostic apparatus S and transfers the received various setting requests to the apparatus body 100. For example, the input device 19 receives various setting requests for controlling the ultrasonic probe 1 and transfers them to the apparatus body 100.

The apparatus body 100 controls the transmission of ultrasonic waves by the ultrasonic probe 1 and the reception of reflected waves by the ultrasonic probe 1. Then, the apparatus body 100 generates ultrasonic images on the basis of the echo signal that has been added for each sub-array from the ultrasonic probe 1, for example. The apparatus body 100, as illustrated in FIG. 1, includes a transmitting and receiving circuit 11, a B-mode processing circuit 12, a Doppler processing circuit 13, a storage circuit 15, and a control circuit 16.

The transmitting and receiving circuit 11 is a transmitting and receiving circuit that, by receiving the control by the control circuit 16, performs transmitting and receiving of drive signals and received signals between the ultrasonic probe 1 and the apparatus body 100. For example, the transmitting and receiving circuit 11 controls the value of the amplitude of the drive signals to the ultrasonic probe 1. The transmitting and receiving circuit 11 controls the amount of transmission delay for the ultrasonic waves transmitted to the ultrasonic probe 1 from the ultrasonic probe 1 (the amount of transmission delay for the ultrasonic wave that each ultrasonic transducer element outputs).

The transmitting and receiving circuit 11 further controls the amount of reception delay for echo signals (the amount of delay for the echo signal that each ultrasonic transducer element received).

The transmitting and receiving circuit 11 further includes an A/D (analog to digital) converter and a receive beamformer. When the transmitting and receiving circuit 11 receives the echo signal (of analog format) added for each sub-array that is output from the ultrasonic probe 1, the A/D converter converts the echo signal of analog format into echo data of digital format. The receive beamformer performs phasing addition processing on the echo data of digital format for each sub-array and generates the echo data having directivity. The receive beamformer transmits the echo data after the phasing addition processing to the B-mode processing circuit 12 and the Doppler processing circuit 13.

The B-mode processing circuit 12 is a processor that generates B-mode data on the basis of the echo data output from the transmitting and receiving circuit 11. That is, the B-mode processing circuit 12 receives the echo data that is output from the transmitting and receiving circuit 11. Then, the B-mode processing circuit 12 performs logarithmic amplification, envelope detection processing, and the like on the received echo data and generates data (B-mode data) for which the signal strength is expressed in brightness.

The Doppler processing circuit 13 is a processor that generates Doppler data on the basis of the echo data output from the transmitting and receiving circuit 11. That is, the Doppler processing circuit 13 receives the echo data that is output from the transmitting and receiving circuit 11. Then, the Doppler processing circuit 13 performs frequency analysis on velocity information from the received echo data, extracts blood flow, tissue, and contrast echo components by the Doppler effect, and generates data (Doppler data) for which moving body information such as the average velocity, dispersion, power, and the like on multiple points has been extracted.

The storage circuit 15 is implemented by a semiconductor memory device such as a RAM (random access memory), a flash memory, and the like, a hard disk, an optical disk, or the like, for example. The storage circuit 15 stores therein ultrasonic images generated, for example. The storage circuit 15 further stores therein data (raw data) output from the B-mode processing circuit 12 and the Doppler processing circuit 13.

Furthermore, the storage circuit 15 stores therein control programs for performing ultrasonic transmitting and receiving, image generation, image processing, and display processing and various data such as diagnostic information (for example, patient's ID, findings of physicians, and the like), diagnostic protocols, various body marks, and the like.

The control circuit 16 is a processor as a CPU that controls the entire processing of the ultrasonic diagnostic apparatus S. For example, the control circuit 16 controls, based on various setting requests input from an operator via the input device 19 and on various control programs and various data read from the storage circuit 15, the transmitting and receiving circuit 11, the B-mode processing circuit 12, and the Doppler processing circuit 13. The control circuit 16 further controls the monitor 18 so as to display ultrasonic images stored in the storage circuit 15 and various images stored in the storage circuit 15, or the GUI for performing image generation processing and various image processing, image generation results, and the like.

Furthermore, the control circuit 16 has an image generation function 16*a* and an image processing function 16*b*. The image generation function 16*a* generates ultrasonic images from the data generated by the B-mode processing circuit 12 and the Doppler processing circuit 13. That is, the image generation function 16*a* generates B-mode images representing the strength of the echo in brightness from the B-mode data generated by the B-mode processing circuit 12. The image generation function 16*a* further generates average velocity images, dispersion images, power images, or color Doppler images as combination images of the foregoing that represent moving body information from the Doppler data generated by the Doppler processing circuit 13. The image processing function 16*b* performs, on the various image data generated, various image processing such as dynamic range, luminance (brightness), contrast, or γ-curve correction, RGB conversion, and the like.

The image generation function 16*a* and the image processing function 16*b* are implemented, as the control circuit 16 as the CPU executes the control program. However, the embodiments are not limited to the relevant example, and a part of or a whole of the image generation function 16*a* and the image processing function 16*b* may be implemented by dedicated hardware designed to execute the same functions, for example, a semiconductor integrated circuit such as ASIC (application-specific integrated circuit), DSP (digital signal processor), FPGA (field-programmable gate array), and the like, or a conventional circuit module and the like.

Ultrasonic Probe

Next, the ultrasonic probe 1 in the first embodiment will be described. In the first embodiment, in order to make the description specific, the ultrasonic probe 1 is exemplified with a sector probe as an ultrasonic probe that deflects the acoustic path. However, it is not intended to be limited to the relevant example, and the embodiment is also applicable to a convex probe, as an ultrasonic probe that similarly deflects the acoustic path.

Figure 2:
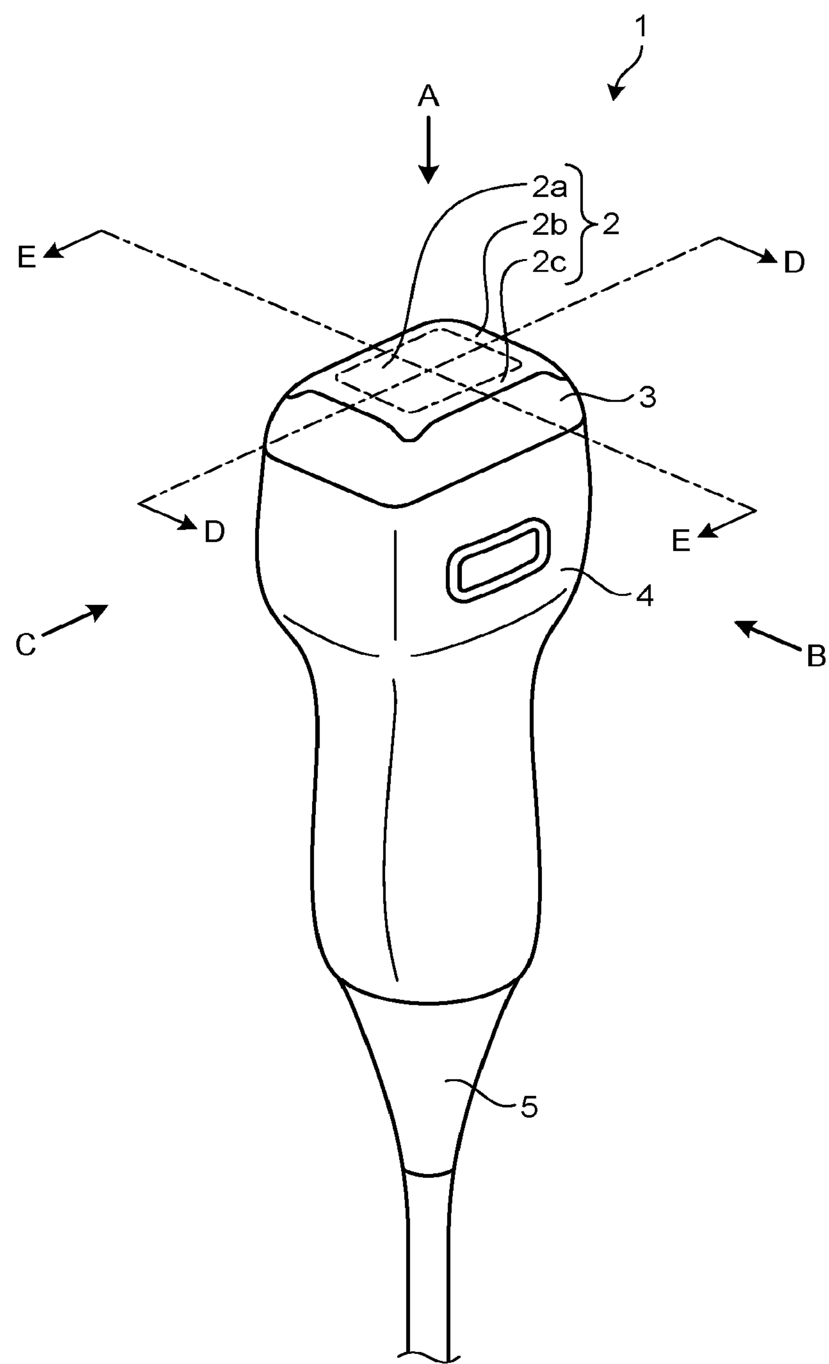
FIG. 2 is a perspective view illustrating one example of the appearance of the ultrasonic probe in the first embodiment.

FIG. 2 is a perspective view illustrating the appearance of the ultrasonic probe 1 in the first embodiment. As illustrated in FIG. 2, the ultrasonic probe 1 includes an offset 2, an exterior member 3, a housing 4, and a connection cable 5.

The offset 2 is provided on an ultrasonic-transmitting and receiving side of a transducer element array composed of a plurality of ultrasonic transducer elements and has a contact portion with a subject. The offset 2 has at least a first region 2*a* that is formed by a curved surface having a first curvature and arranged in the middle of the contact portion and a second region 2*b* that is formed by a curved surface having a second curvature greater than the first curvature and arranged on an edge of the contact portion.

That is, the offset 2 is an elastic member to prevent multiple reflections and the like and to improve acoustic characteristics, by ensuring the distance between the ultrasonic transducer elements and the body surface, and the contact properties with the body surface. The offset 2 has the first region 2*a* that is arranged in the middle of the contact portion as a curved surface having a first curvature or a plane surface, the second regions 2*b* that are arranged on the edges of the contact portion along a first direction (for example, longitudinal direction) of the ultrasonic-transducer element array as curved surfaces having a second curvature, and third regions 2*c* that are arranged on the edges of the contact portion along a second direction (for example, lateral direction) intersecting with the first direction of the ultrasonic-transducer element array as curved surfaces having a third curvature that is different from the second curvature. In FIG. 2 and others, for the convenience of description, the contour of the first region 2*a* is indicated by a dashed-dotted line.

In the first embodiment, a plane surface is defined as a curved surface for which the curvature is 0 (zero). In the following description, in order to make the description specific, a case in which the first region 2*a* is a plane surface (that is, a case in which the first region 2*a* is a curved surface of the first curvature=0) will be exemplified. Furthermore, the (body) contact surface of the offset 2 is formed by the respective surfaces of the first region 2*a*, the second region 2*b*, and the third region 2*c*.

The exterior member 3 supports the offset. That is, the exterior member 3 has an opening that is shaped along the contour of the offset 2. The exterior member 3 is a supporting member that supports the side surfaces of the offset 2 that is fitted in this opening and exposing a portion thereof. The exterior member 3 is formed of resin, plastic, and the like.

The housing 4 incorporates a plurality of ultrasonic transducer elements, the backing material, and an electronic circuit and wiring that are connected to the ultrasonic transducer elements, while the exterior member 3 for which the offset 2 is fitted in is attached. The user such as a clinical technologist, a doctor, and the like performs ultrasonic transmitting and receiving and performs ultrasonic imaging while holding the housing 4 and while bringing the contact surface of the offset 2 that is formed of the first region 2*a*, the second regions 2*b*, and the third regions 2*c* into contact with the surface of the subject.

The connection cable 5 electrically connects the ultrasonic probe 1 and the ultrasonic diagnostic apparatus body 100.

Figure 3:
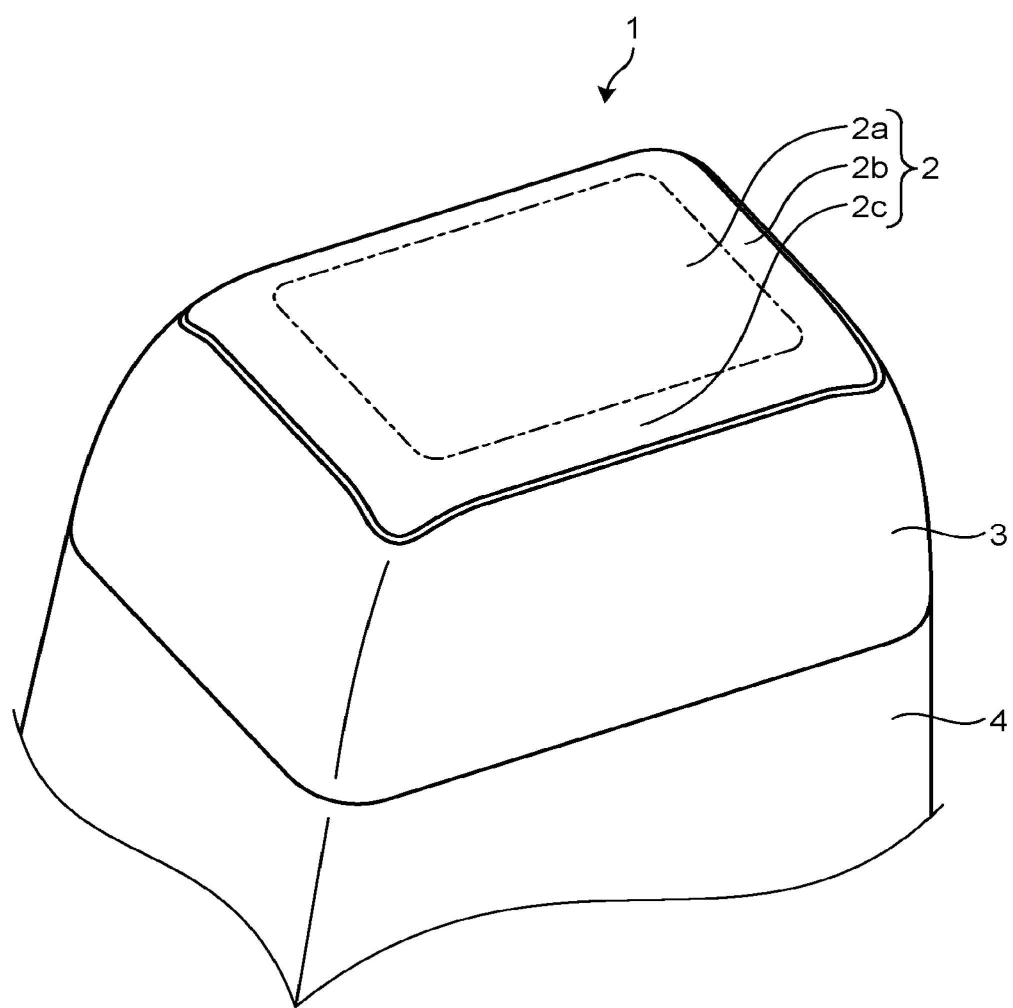
FIG. 3 is a perspective view in which a part of an offset and an exterior member of the ultrasonic probe illustrated in FIG. 2 has been enlarged.
Figure 4:
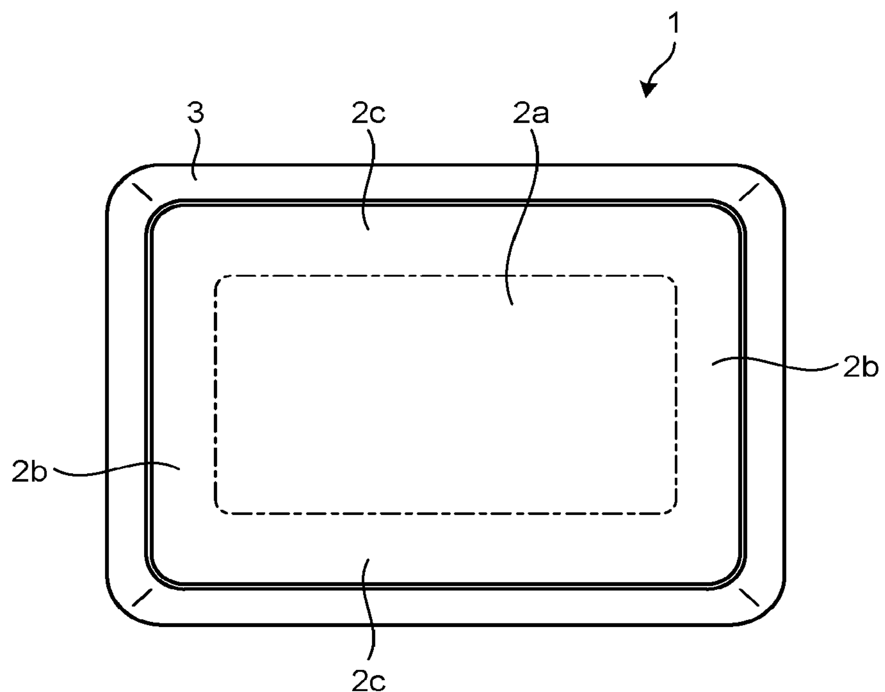
FIG. 4 is a top view of the ultrasonic probe illustrated in FIG. 2 viewed from the A direction.
Figure 5:
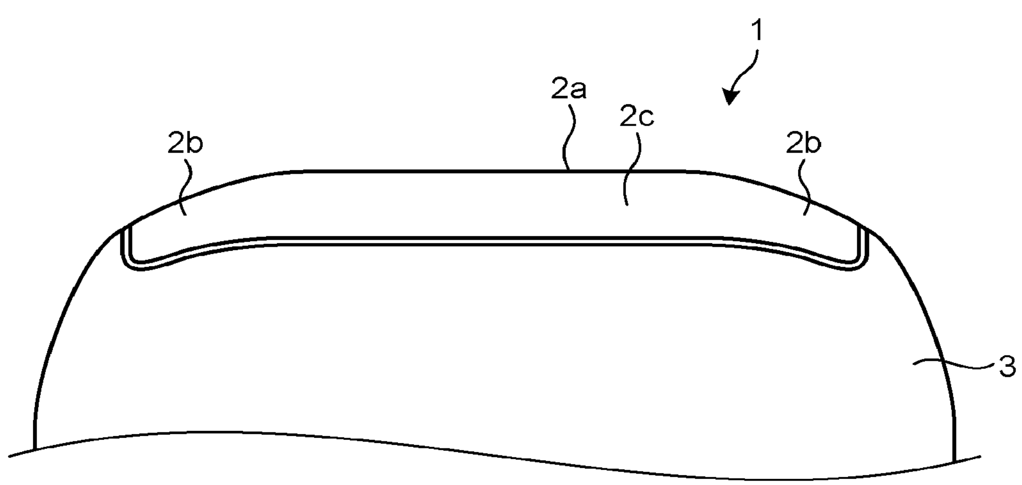
FIG. 5 is a side view of the ultrasonic probe illustrated in FIG. 2 viewed from the B direction.
Figure 6:
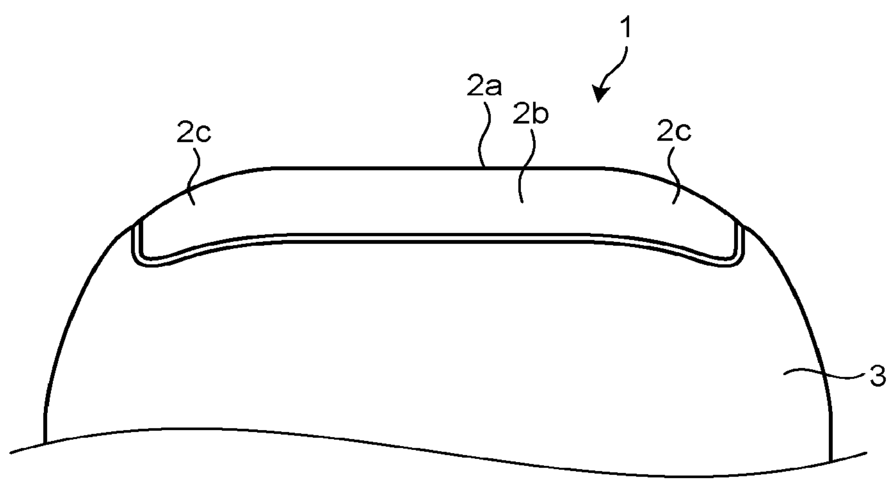
FIG. 6 is a side view of the ultrasonic probe illustrated in FIG. 2 viewed from the C direction.

FIG. 3 is a perspective view in which a part of the offset 2 and the exterior member 3 of the ultrasonic probe 1 illustrated in FIG. 2 has been enlarged. FIG. 4 is a top view of the ultrasonic probe 1 illustrated in FIG. 2 viewed from the A direction (that is, viewed from the location facing the first region 2*a* of the offset 2). FIG. 5 is a side view of the ultrasonic probe 1 illustrated in FIG. 2 viewed from the B direction. FIG. 6 is a side view of the ultrasonic probe 1 illustrated in FIG. 2 viewed from the C direction.

As illustrated in the respective drawings of FIG. 3, FIG. 4, FIG. 5, and FIG. 6, the offset 2 has the first region 2*a* as a plane surface of a rectangular shape, the second regions 2*b* that form the edge portions (of the body contact portion) of the offset 2 along the lateral direction of the first region 2*a*, and the third regions 2*c* that form the edge portions (of the body contact portion) of the offset 2 along the longitudinal direction of the first region 2*a*.

The exterior member 3 has, at each boundary with the offset 2, the same curvature as the curvature of the second region 2*b* or the third region 2*c*. This makes it possible to eliminate steps between the exterior member 3 and the offset 2.

Figure 7:
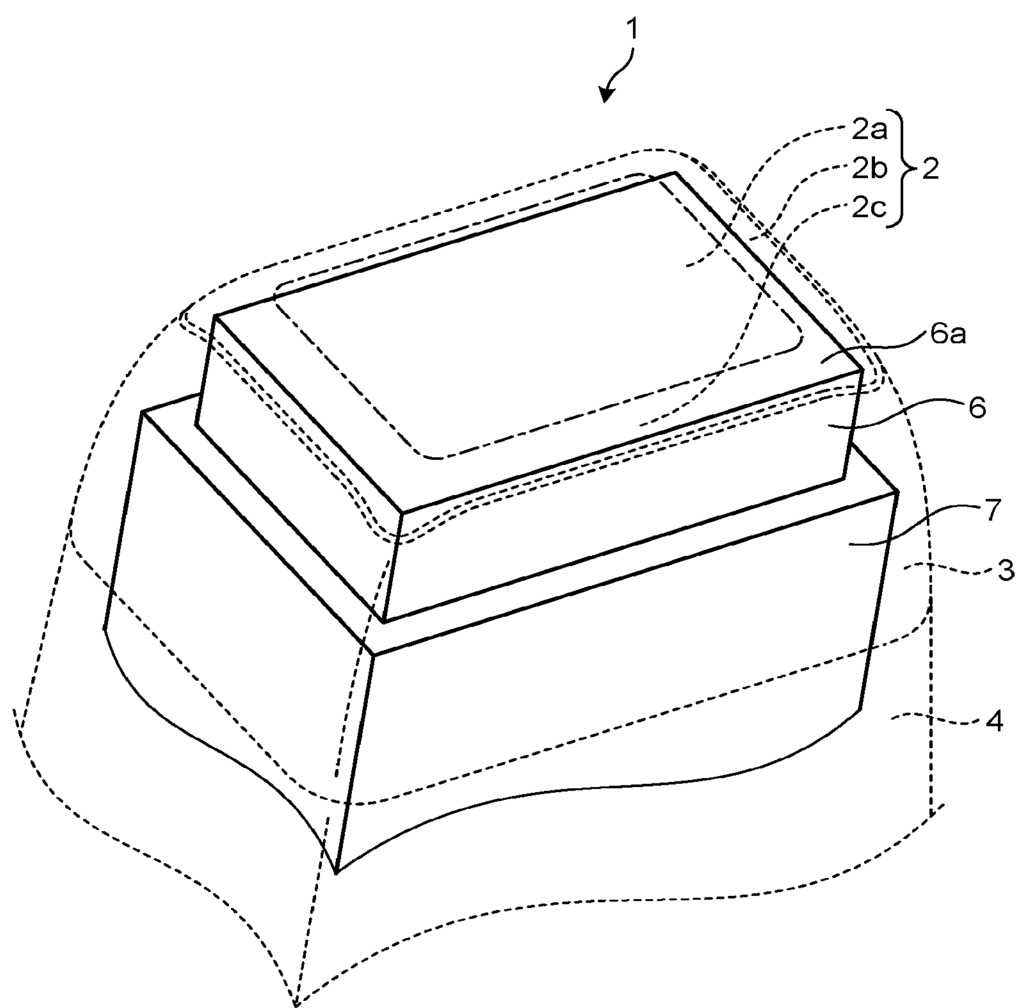
FIG. 7 is a diagram illustrating one example of the positional relation among a first region, second regions, and third regions of the offset and a transducer element array that is incorporated in the ultrasonic probe.

FIG. 7 is a diagram for explaining the positional relation among the first region 2*a*, the second regions 2*b*, and the third regions 2*c* of the offset 2 and the transducer element array 6 that is incorporated in the ultrasonic probe 1. For the convenience of description, in FIG. 7, the internal structure of the ultrasonic probe 1 is indicated by solid lines, and the offset 2 and a part of the exterior member 3 (that is a portion indicated by the solid line in FIG. 3) are indicated by dotted lines.

As illustrated in FIG. 7, the ultrasonic probe 1 incorporates the transducer element array 6 and a backing material 7. The transducer element array 6 is formed by a plurality of ultrasonic transducer elements that are two-dimensionally arranged in a lattice form, for example. The first region 2*a* of the offset 2 is located above the upper surface (surface on the ultrasonic-transmitting and receiving side) 6*a* of the transducer element array 6. The first region 2*a* of the offset 2 is included in the upper surface of the transducer element array 6, and thus, the area of the first region 2*a* of the offset 2 is smaller as compared with the area of the upper surface of the transducer element array 6. The second region 2*b* and the third region 2*c* of the offset 2 are each provided such that a part thereof overlaps the first region 2*a* of the transducer element array 6.

Figure 8:
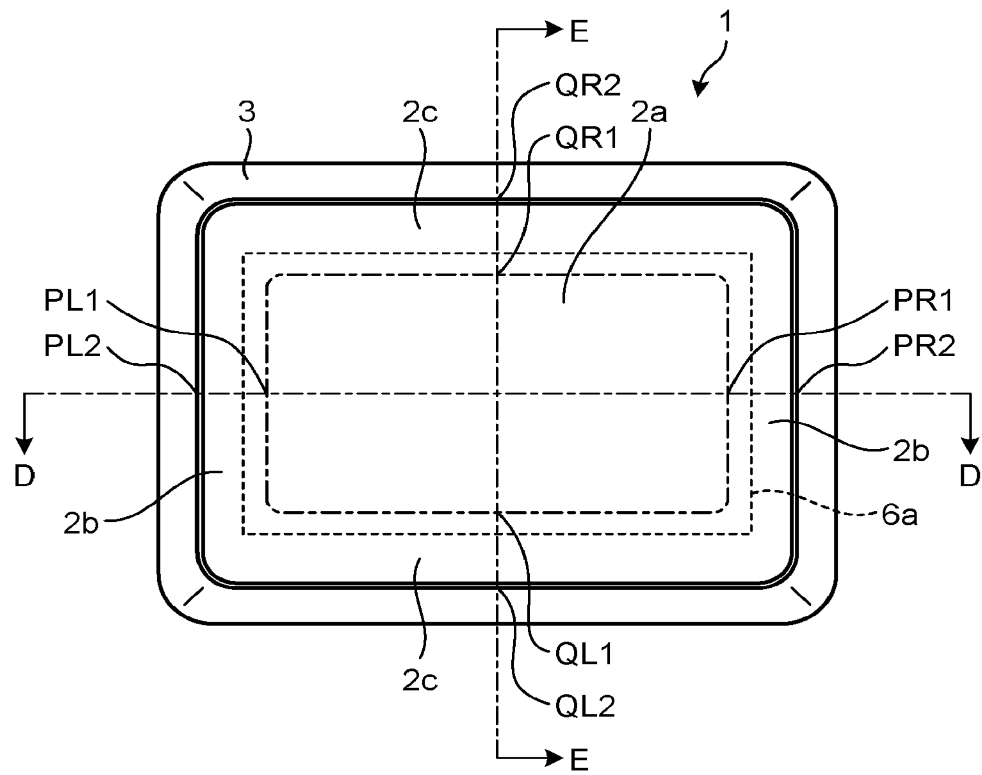
FIG. 8 is a diagram in which, in the top view illustrated in FIG. 4, the contour of an upper surface of the transducer element array has been appended by a dotted line.
Figure 9:
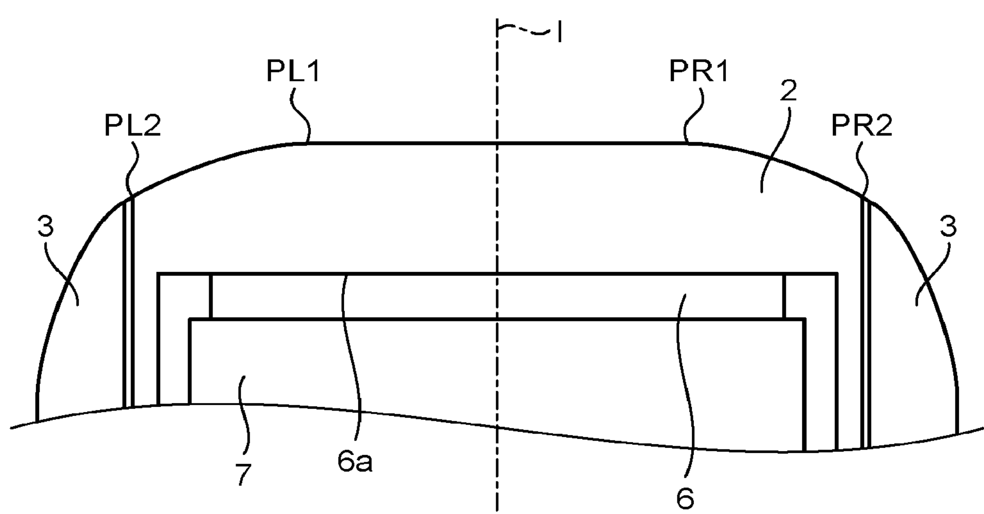
FIG. 9 is a cross-sectional view taken along the line D-D (along the longitudinal direction) of the ultrasonic probe illustrated in FIG. 2 and FIG. 8.
Figure 10:
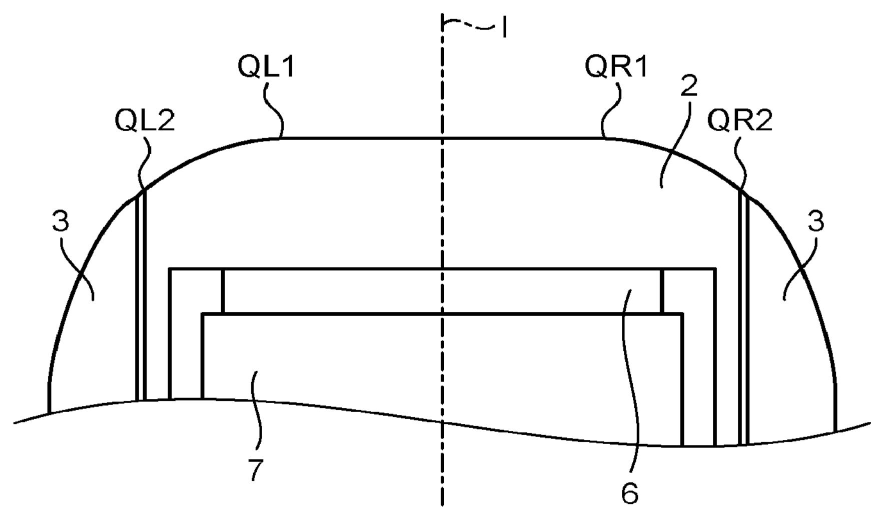
FIG. 10 is a cross-sectional view taken along the line E-E (along the lateral direction) of the ultrasonic probe illustrated in FIG. 2 and FIG. 8.

FIG. 8 is a diagram in which, in the top view illustrated in FIG. 4, the contour of the upper surface 6*a* of the transducer element array 6 (that is, the surface on the ultrasonic-transmitting and receiving side of the transducer element array 6) has been appended by a dotted line. FIG. 9 is a cross-sectional view taken along the line D-D (along the longitudinal direction) of the ultrasonic probe 1 illustrated in FIG. 2 and FIG. 8. FIG. 10 is a cross-sectional view taken along the line E-E (along the lateral direction) of the ultrasonic probe 1 illustrated in FIG. 2 and FIG. 8. The straight line 1 indicated by a dashed-dotted line in FIG. 9 and FIG. 10 is a central axis of the cross-section taken along the line D-D or E-E of the ultrasonic probe 1. The cross-sections illustrated in FIG. 9 and FIG. 10 are an example, and it is not intended to limit the cross-sectional shape of the ultrasonic probe 1 in the first embodiment.

In FIG. 8 and FIG. 9, a position PL1 (and the dashed-dotted line including the position PL1) corresponds to the boundary (that is, a discontinuous point or discontinuity line of curvature) between the first region 2*a* and the second region 2*b*. Similarly, a position PR1 (and the dashed-dotted line including the position PR1) corresponds to the boundary (that is, a discontinuous point or discontinuity line of curvature) between the first region 2*a* and the second region 2*b*. The first region 2*a* as a plane surface is formed extending from the position PL1 to the position PR1 on the surface of the offset 2. The second regions 2*b* having the second curvature are formed, on the left side, in a range between the position PL1 as the starting point and an edge position PL2 of the offset 2 as the end-point, and on the right side, in a range between the position PR1 as the starting point and an edge position of the offset 2 as the end-point PR2.

Similarly, as illustrated in FIG. 8 and FIG. 10, a position QL1 (and the dashed-dotted line including the position QL1) corresponds to the boundary (that is, a discontinuous point or discontinuity line of curvature) between the first region 2*a* and the third region 2*c*. Likewise, a position QR1 (and the dashed-dotted line including the position QR1) corresponds to the boundary (that is, a discontinuous point or discontinuity line of curvature) between the first region 2*a* and the third region 2*c*. The first region 2*a* as a plane surface is formed extending from the position QL1 to the position QR1 on the surface of the offset 2. The third regions 2*c* having the third curvature are formed, on the left side, in a range between the position QL1 as the starting point and an edge position of the offset 2 as the end-point QL2, and on the right side, in a range between the position QR1 as the starting point and an edge position QR2 of the offset 2 as the end-point.

That is, the second regions 2*b* and the third regions 2*c* are formed, in the cross-section of the ultrasonic probe 1, in a range where the starting points PL1 and QL1 are present within a range to which the external form of the transducer element array 6 is projected on the body contact surface of the offset 2 and where the edge positions of the offset 2 are the end-points PL2 and QL2. The first region 2*a* as a plane surface is formed extending from the position PL1 to the position PR1 in the longitudinal direction and is formed extending from the position QL1 to the position QR1 in the lateral direction. Thus, the surface (body contact surface) of the offset 2 is formed by the combination of a plane surface and two curved surfaces of different curvature (or combination of three curved surfaces of different curvature).

The second curvature and the third curvature are determined, for example, by at least one of body contact properties, the type (sector probe, convex probe, and the like) and size of the probe, the size of the transducer element array 6, a maximum deflection angle, and the like as a reference, on the assumption that the second regions 2*b* and the third regions 2*c* are connected to the first region 2*a* as a plane surface.

As in the foregoing, the ultrasonic probe according to the first embodiment includes the ultrasonic-transducer element array 6 formed by a plurality of ultrasonic transducer elements, the offset 2 provided on the ultrasonic-transmitting and receiving side of the ultrasonic-transducer element array 6 and having the contact portion with a subject, and the exterior member 3 configured to support the offset 2. The offset 2 has at least the first region 2*a* that is formed by a curved surface having the first curvature and arranged in the middle of the contact portion, and the second regions 2*b* that are formed by a curved surface having the second curvature greater than the first curvature and arranged on the edges of the contact portion.

That is, the second region 2*b* arranged at the edge of the contact portion of the offset 2 has the second curvature greater than the first curvature of the first region 2*a* located in the middle. Thus, at the edges of the contact portion of the offset 2, the offset 2 can be made small as compared with the conventional one, and downsizing of the footprint can be achieved. Furthermore, the acoustic path of the maximum deflection angle at the edge of the contact portion of the offset 2 can be made short as compared with the conventional one, and the energy loss (attenuation) due to in-offset attenuation can be reduced.

In addition, along with downsizing of the offset 2, the opening in the exterior member 3 to which the offset 2 is fitted in and that exposes a portion thereof can be made small. As a result, downsizing of the footprint combining not only the offset 2 but also the exterior member 3 can be achieved.

Comparative Example

A comparative example between the ultrasonic probe in the first embodiment and a conventional typical ultrasonic probe will be described. In the following comparative example, the size of the footprint and an acoustic path distance are compared in the longitudinal direction as an example. The result in the lateral direction will be the same as that in the longitudinal direction, and thus the description thereof is omitted.

Figure 11:
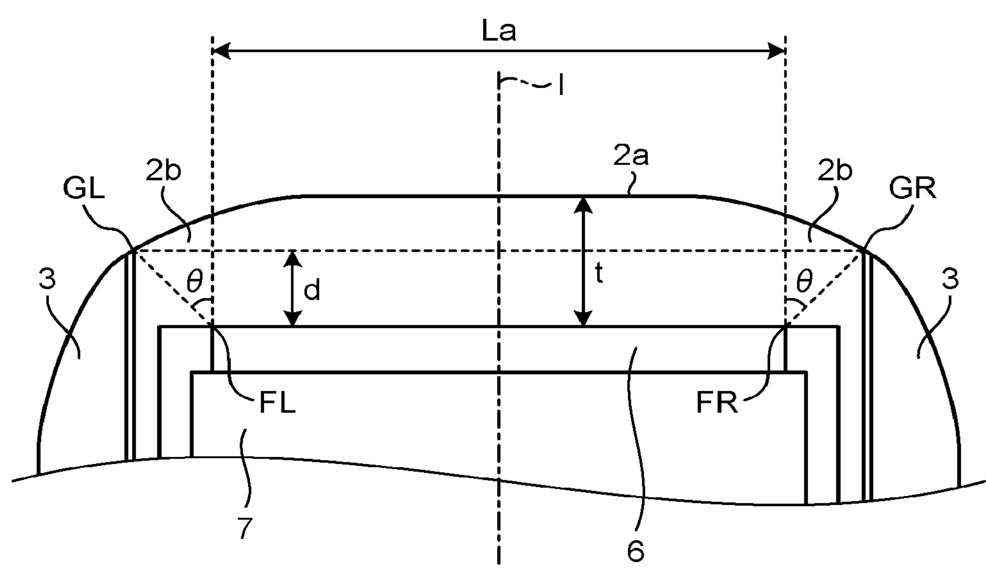
FIG. 11 is a diagram for explaining acoustic characteristics achieved by the ultrasonic probe having the offset and is a cross-sectional view taken along the line D-D (longitudinal direction) of the ultrasonic probe illustrated in FIG. 2 and FIG. 8.

FIG. 11 is a diagram for explaining the acoustic characteristics achieved by the ultrasonic probe 1 having the offset 2 and is a cross-sectional view taken along the line D-D (longitudinal direction) of the ultrasonic probe 1 illustrated in FIG. 2 and FIG. 8.

An effective ultrasonic-transducer element group (that is, an ultrasonic-transducer element group used for actual ultrasonic transmitting and receiving) is assumed to be the entire transducer element array 6, for example. In this case, the acoustic path from the effective ultrasonic-transducer element group is transmitted (acoustic irradiation) with the maximum deflection angle θ as the outermost side.

It is defined that the length of the effective ultrasonic-transducer element group in the longitudinal direction is La, the needed thickness near the center of the offset 2 (that is, in the first region 2*a*) is t, and the needed thickness near the edge of the offset 2 (that is, at the end-point of the second region 2*b*) is d (however, d<t). In such a case, the length of the offset 2 in the longitudinal direction is La+2×d×tan θ. The acoustic path distance from the end portion FL (FR) of the effective ultrasonic-transducer element group to the acoustic-irradiation open-end GL (GR) (that is, acoustic path distance in the maximum deflection angle θ) is d×(1/cos θ).

Figure 12:
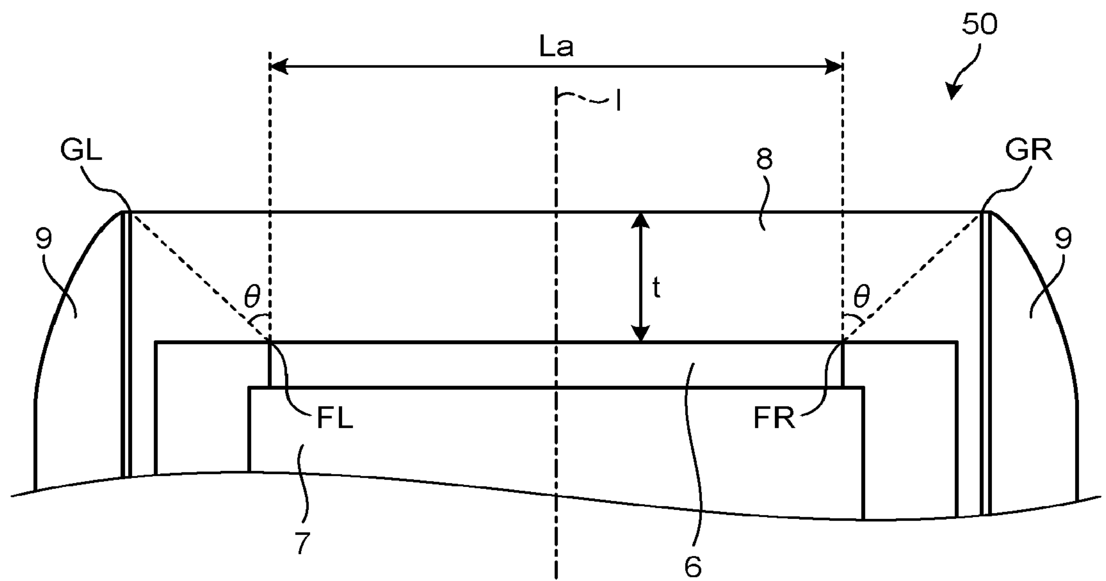
FIG. 12 is a cross-sectional view taken along the longitudinal direction of a conventional typical ultrasonic probe.

FIG. 12 is a cross-sectional view taken along the longitudinal direction of a conventional typical ultrasonic probe 50. It is assumed that the ultrasonic probe 50 incorporates the transducer element array 6 and the backing material 7 the same as those of the ultrasonic probe 1 in the first embodiment. The conventional typical ultrasonic probe 50 includes an exterior member 9.

As illustrated in FIG. 12, an offset 8 has a uniform thickness over the longitudinal direction. It is defined that the length of the effective ultrasonic-transducer element group in the longitudinal direction is La and the needed thickness of the offset 8 is t. In such a case, the length of the offset 8 in the longitudinal direction is La+2×t×tan θ. The acoustic path distance from the end portion FL (FR) of the effective ultrasonic-transducer element group to the acoustic-irradiation open-end GL (GR) (that is, acoustic path distance in the maximum deflection angle θ) is t×(1/cos θ).

That is, when compared with the conventional typical ultrasonic probe 50, the ultrasonic probe 1 in the first embodiment achieves downsizing of the footprint for the difference in size between the offset 2 and the offset 8, ΔL=2 (t−d)tan θ.

Furthermore, the acoustic path distance on the acoustic path of the maximum deflection angle θ in the ultrasonic probe 1 in the first embodiment is d×(1/cos θ), and the acoustic path distance on the acoustic path of the maximum deflection angle θ in the conventional typical ultrasonic probe 50 is t×(1/cos θ). Thus, the distance reduction for the difference, (t−d)<(1/cos θ), in acoustic path distance on the acoustic path of the maximum deflection angle θ is achieved, and the energy loss due to in-offset attenuation can be reduced.

First Modification

In the above-described discussion, it has been described that the first region 2*a* located in the middle of the offset 2 is of a plane region having the first curvature=0 and that the surface of the offset 2 has a shape for which the plane surface and two curved surfaces of different curvature are combined. However, the first region 2*a* located near the middle of the offset may be not the plane surface (not the first curvature=0) but a curved surface. In this case, the offset 2 is configured by a combination of three curved surfaces of different curvature. In other words, when the first region 2*a* is made to be a curved surface that is not the first curvature=0, the offset 2 is configured by curved surfaces having discontinuous curvature extending from the middle to the edges in the lateral direction and extending from the middle to the edges in the longitudinal direction. In such a configuration, the first region 2*a* is preferable to be in a gentle curve, relative to the second region 2*b* and the third region 2*c*. Thus, the first curvature is preferable to be of a small value relative to the second curvature and the third curvature.

The value of each of the first curvature, the second curvature, and the third curvature can be determined by at least one of body contact properties, the type (sector probe, convex probe, and the like) and size of the probe, the size of the transducer element array 6, the maximum deflection angle, and the like as a reference.

Second Modification

Figure 13:
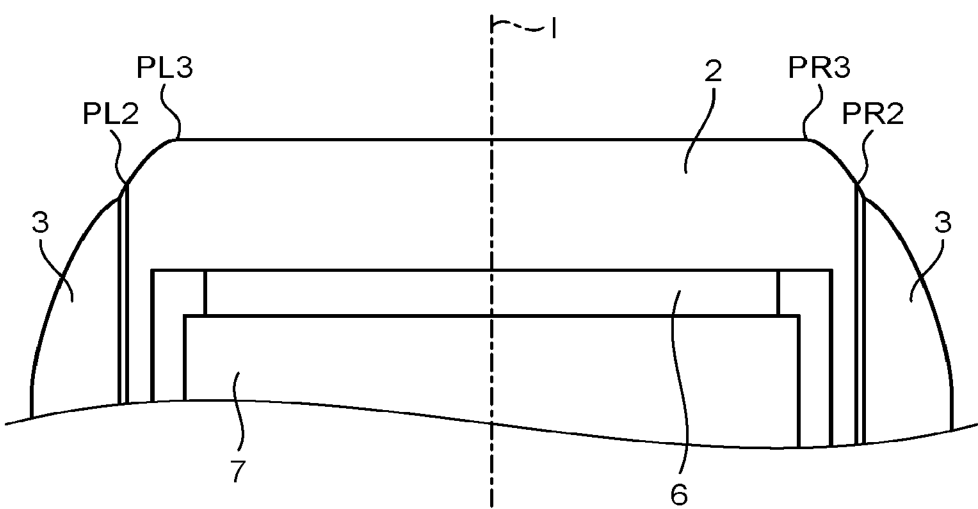
FIG. 13 is a diagram for explaining a second modification and is a cross-sectional view taken along the line D-D (along the longitudinal direction) of the ultrasonic probe illustrated in FIG. 2 and FIG. 8.
Figure 14:
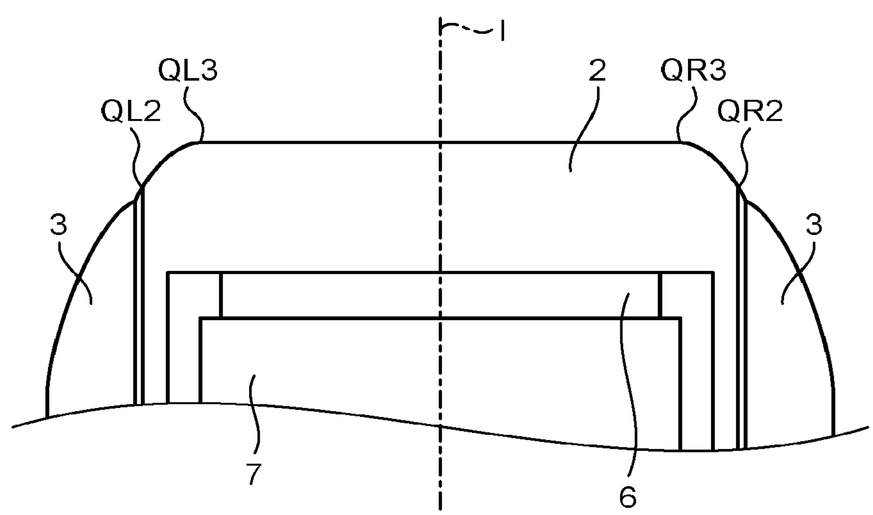
FIG. 14 is a diagram for explaining the second modification and is a cross-sectional view taken along the line E-E (along the lateral direction) of the ultrasonic probe illustrated in FIG. 2 and FIG. 8.

In the above-described discussion, the case in which the boundaries between the first region 2*a* and the second regions 2*b* and between the first region 2*a* and the third regions 2*c* (that is, discontinuous points or discontinuity lines of curvature) are present within the range where the external form (upper surface 6*a*) of the transducer element array 6 is projected on the body contact surface of the offset 2 has been exemplified. Meanwhile, as illustrated in FIG. 13 and FIG. 14, the boundaries between the first region 2*a* and the second regions 2*b* and between the first region 2*a* and the third regions 2*c* (in FIG. 13 and FIG. 14, curvature discontinuous points PL3, PR3, QL3, QR3) may be made to be present outside the range where the external form (upper surface 6*a*) of the transducer element array 6 is projected on the body contact surface of the offset 2. In this case, the second curvature of the second region 2*b*, the third curvature of the third region 2*c*, and the curvature of the exterior member 3 are larger as compared with the case in which the boundaries between the first region 2*a* and the second regions 2*b* and between the first region 2*a* and the third regions 2*c* are present within the range where the external form of the transducer element array 6 is projected on the body contact surface of the offset 2 (that is, the case illustrated in FIG. 9 and FIG. 10).

The positions where the boundaries between the first region 2*a* and the second regions 2*b* and between the first region 2*a* and the third regions 2*c* are placed on the surface of the offset 2 are determined by at least one of body contact properties, the type (sector probe, convex probe, and the like) and size of the probe, the size of the transducer element array 6, the maximum deflection angle, and the like as a reference.

Third Modification

In the above-described discussion, the reason why the first region 2*a* as a plane region of the offset 2 is rectangular is that the transducer element array 6 is rectangular parallelepiped (that is, the upper surface 6*a* of the transducer element array 6 is rectangular). Thus, in the offset 2 of the ultrasonic probe 1 illustrated in FIG. 2 to FIG. 11, it has been exemplified that the second curvature of the second region 2*b* and the third curvature of the third region 2*c* are of different values. However, the embodiment is not limited to the relevant example, and the second curvature of the second region 2*b* and the third curvature of the third region 2*c* may be of the same value.

Fourth Modification

In the above-described discussion, the case in which the ultrasonic probe 1 is a two-dimensional array probe for which a plurality of ultrasonic transducer elements are two-dimensionally arranged in a lattice form has been exemplified. However, the embodiment is not limited to the relevant example, and is applicable, as necessary, even if the ultrasonic probe 1 is a one-dimensional array probe or a 1.5-dimensional array probe. For example, if the ultrasonic probe 1 is a one-dimensional array probe, the offset has the configuration in which the second region 2*b* is provided on both sides in the longitudinal direction of the first region 2*a* located in the middle and in which no third region is present. If the ultrasonic probe 1 is a 1.5-dimensional array probe, it has a configuration in which no third region is provided as with the case of a one-dimensional array probe, or a configuration that has a third region having a larger third curvature relative to the case of a two-dimensional array probe.

Fifth Modification

In recent years, an ultrasonic probe incorporating a transmitting and receiving circuit, a signal processing circuit, and the like (that is, a probe incorporating a part of or a whole of the configuration of the apparatus body 100 illustrated in FIG. 1) has been developed. A fifth modification is an example in which the configuration of the first embodiment is applied to such an ultrasonic probe.

That is, the configuration including the offset 2 and the exterior member 3 is the same as that of the ultrasonic probe 1 in the first embodiment, and inside the housing 4, a part of or the whole of the transmitting and receiving circuit 11, the B-mode processing circuit 12, the Doppler processing circuit 13, the storage circuit 15, and the control circuit 16 may be incorporated. Typical examples include a configuration for which the ultrasonic probe 1 incorporates the whole of the transmitting and receiving circuit 11, the B-mode processing circuit 12, the Doppler processing circuit 13, the storage circuit 15, and the control circuit 16 and that, by connecting it to a tablet computer equipped with the monitor 18 and the input device 19, implements the ultrasonic diagnostic apparatus S, or a configuration for which the ultrasonic probe 1 incorporates a part of the transmitting and receiving circuit 11, the B-mode processing circuit 12, the Doppler processing circuit 13, the storage circuit 15, and the control circuit 16 and that, by connecting it to a tablet computer equipped with the image generation function 16*a*, the image processing function 16*b*, the monitor 18, and the input device 19, implements the ultrasonic diagnostic apparatus S.

The ultrasonic probe 1 in the fifth modification can be regarded as an ultrasonic diagnostic apparatus also, because the transmitting and receiving circuit, the signal processing circuit, and the like are incorporated.

Second Embodiment

Next, an ultrasonic probe attachment and an ultrasonic probe assembly according to a second embodiment will be described.

Figure 15:
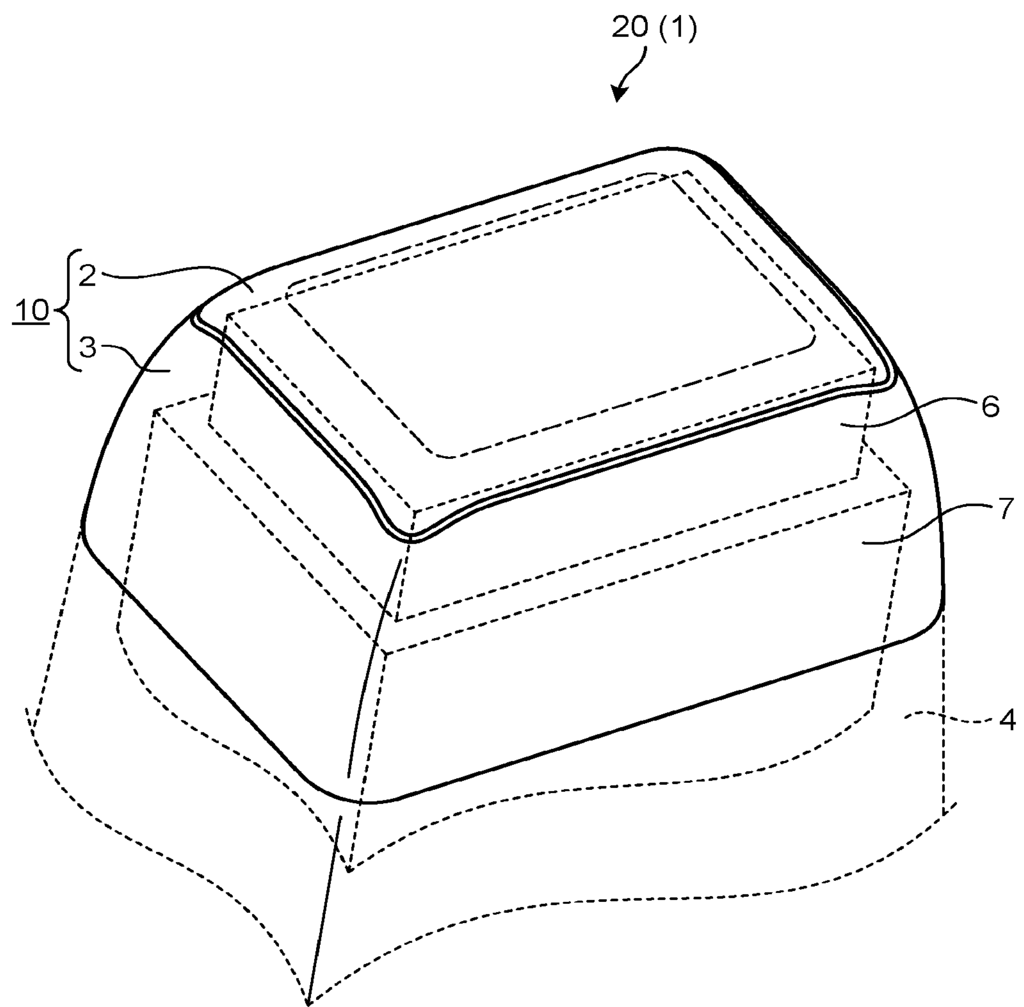
FIG. 15 is a diagram illustrating one example of an ultrasonic probe attachment and an ultrasonic probe assembly according to a second embodiment.

FIG. 15 is a diagram illustrating an ultrasonic probe attachment 10 and an ultrasonic probe assembly 20 in the second embodiment.

In this case, the ultrasonic probe attachment 10 is made up of the offset 2, and the exterior member 3 described in the first embodiment. The ultrasonic probe attachment 10 is detachable with respect to the housing 4 of the ultrasonic probe. The ultrasonic probe assembly 20 is made up of an ultrasonic probe that does not have the offset 2 and the exterior member 3 (that is, has no ultrasonic probe attachment 10), and the ultrasonic probe attachment 10. Thus, the ultrasonic probe 1 in the first embodiment is substantively in the same configuration as the ultrasonic probe assembly 20.

According to the ultrasonic probe attachment 10 in the above-described second embodiment, it can be attached to the housing of an existing ultrasonic probe, for example. As a result, on the existing ultrasonic probe, the ex-post facto improvement can be made, as the ultrasonic probe assembly 20 having the offset 2 and the exterior member 3.

The term "processor" used in the above description means a CPU (central processing unit), a GPU (graphics processing unit), or a circuit such as an ASIC (application-specific integrated circuit) and a programmable logic device (for example, an SPLD (simple programmable logic device), a CPLD (complex programmable logic device), an FPGA (field-programmable gate array), and the like), for example. The processor implements functions by reading out and executing the programs stored in the storage circuit. Instead of storing the programs in the storage circuit, it does not matter even if the programs are directly incorporated in the circuitry of the processor. In this case, the processor implements the functions by reading out and executing the programs incorporated in the circuitry. Each processor in the embodiments is not limited to the case of being configured as a single circuitry for each processor, and may be configured as a single processor by combining a plurality of independent circuitries so as to implement its functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic probe comprising:
an ultrasonic-transducer element array that is formed by a plurality of ultrasonic transducer elements;
an offset provided on an ultrasonic-transmitting and receiving side of the ultrasonic-transducer element array, and including a contact portion with a subject; and
an exterior member configured to support the offset, wherein
the offset has at least:
a first region being located in a middle of the contact portion and formed by a surface having a first curvature, and
a second region being located on an edge of the contact portion and formed by a surface having a second curvature greater than the first curvature,
the exterior member is provided adjacent to the second region, and
a surface formed by the exterior member has a curvature greater than the first curvature.

2. The ultrasonic probe according to claim 1, wherein
the ultrasonic-transducer element array is formed by the ultrasonic transducer elements that are two-dimensionally arranged in a lattice form, and
the offset includes the second region at an edge of the contact portion along a first direction of the ultrasonic-transducer element array and, at an edge of the contact portion along a second direction intersecting with the first direction of the ultrasonic-transducer element array, further includes a third region that is formed by a surface having a third curvature that is greater than the first curvature and different from the second curvature.

3. The ultrasonic probe according to claim 2, wherein the first curvature is zero and the first region is a plane surface.

4. The ultrasonic probe according to claim 3, wherein the second region has a starting point that is present within a range where an external form of the ultrasonic-transducer element array is projected on the contact portion of the offset, and has an end-point at an edge of the contact portion of the offset.

5. The ultrasonic probe according to claim 3, wherein a boundary between the first region and the second region is included in a region where a surface on the ultrasonic-transmitting and receiving side of the ultrasonic-transducer element array is projected on the contact portion.

6. The ultrasonic probe according to claim 3, wherein a boundary between the first region and the second region is present outside a region where a surface on the ultrasonic-transmitting and receiving side of the ultrasonic-transducer element array is projected on the contact portion.

7. The ultrasonic probe according to claim 3, wherein the exterior member has the second curvature at a boundary between the offset and the exterior member.

8. The ultrasonic probe according to claim 3, wherein the exterior member has an opening shaped along a contour of the offset and is configured to support a side surface of the offset that is fitted in the opening and exposing a portion thereof.

9. The ultrasonic probe according to claim 2, wherein the second region has a starting point that is present within a range where an external form of the ultrasonic-transducer element array is projected on the contact portion of the offset, and has an end-point at an edge of the contact portion of the offset.

10. The ultrasonic probe according to claim 2, wherein a boundary between the first region and the second region is included in a region where a surface on the ultrasonic-transmitting and receiving side of the ultrasonic-transducer element array is projected on the contact portion.

11. The ultrasonic probe according to claim 2, wherein a boundary between the first region and the second region is present outside a region where a surface on the ultrasonic-transmitting and receiving side of the ultrasonic-transducer element array is projected on the contact portion.

12. The ultrasonic probe according to claim 2, wherein the exterior member has the second curvature at a boundary between the offset and the exterior member.

13. The ultrasonic probe according to claim 2, wherein the exterior member has an opening shaped along a contour of the offset and is configured to support a side surface of the offset that is fitted in the opening and exposing a portion thereof.

14. The ultrasonic probe according to claim 1, wherein the first curvature is zero and the first region is a plane surface.

15. The ultrasonic probe according to claim 14, wherein the second region has a starting point that is present within a range where an external form of the ultrasonic-transducer element array is projected on the contact portion of the offset, and has an end-point at an edge of the contact portion of the offset.

16. The ultrasonic probe according to claim 14, wherein a boundary between the first region and the second region is included in a region where a surface on the ultrasonic-transmitting and receiving side of the ultrasonic-transducer element array is projected on the contact portion.

17. The ultrasonic probe according to claim 14, wherein a boundary between the first region and the second region is present outside a region where a surface on the ultrasonic-transmitting and receiving side of the ultrasonic-transducer element array is projected on the contact portion.

18. The ultrasonic probe according to claim 14, wherein the exterior member has the second curvature at a boundary between the offset and the exterior member.

19. The ultrasonic probe according to claim 14, wherein the exterior member has an opening shaped along a contour of the offset and is configured to support a side surface of the offset that is fitted in the opening and exposing a portion thereof.

20. The ultrasonic probe according to claim 1, wherein the second region has a starting point that is present within a range where an external form of the ultrasonic-transducer element array is projected on the contact portion of the offset, and has an end-point at an edge of the contact portion of the offset.

21. The ultrasonic probe according to claim 1, wherein a boundary between the first region and the second region is included in a region where a surface on the ultrasonic-transmitting and receiving side of the ultrasonic-transducer element array is projected on the contact portion.

22. The ultrasonic probe according to claim 1, wherein a boundary between the first region and the second region is present outside a region where a surface on the ultrasonic-transmitting and receiving side of the ultrasonic-transducer element array is projected on the contact portion.

23. The ultrasonic probe according to claim 1, wherein the exterior member has the second curvature at a boundary between the offset and the exterior member.

24. The ultrasonic probe according to claim 1, wherein the exterior member has an opening shaped along a contour of the offset and is configured to support a side surface of the offset that is fitted in the opening and exposing a portion thereof.

25. An ultrasonic probe attachment provided on an ultrasonic-transmitting and receiving side of an ultrasonic-transducer element array formed by a plurality of ultrasonic transducer elements in an ultrasonic probe, the ultrasonic probe attachment comprising:

an offset including a contact portion with a subject; and an exterior member configured to support the offset, wherein the offset has at least:

a first region being located in a middle of the contact portion and formed by a surface having a first curvature, and a second region being located on an edge of the contact portion and formed by a surface having a second curvature greater than the first curvature, the exterior member is provided adjacent to the second region, and a surface formed by the exterior member has a curvature greater than the first curvature.

* * * * *